United States Patent [19]

Ananthasubramanian et al.

[11] Patent Number: 5,705,394
[45] Date of Patent: Jan. 6, 1998

[54] TAGGED EPICHLOROHYDRIN-DIMETHYLAMINE COPOLYMERS FOR USE IN WASTEWATER TREATMENT

[75] Inventors: Sivakumar Ananthasubramanian; Jitendra T. Shah, both of Naperville; Jeffrey R. Cramm, Winfield, all of Ill.

[73] Assignee: Nalco Chemical Company, Naperville, Ill.

[21] Appl. No.: 572,937

[22] Filed: Dec. 15, 1995

Related U.S. Application Data

[63] Continuation-in-part of Ser. No. 423,598, Apr. 17, 1995, abandoned.

[51] Int. Cl.$^6$ ............................................ G01N 21/75
[52] U.S. Cl. .................... 436/55; 436/56; 422/62; 422/3; 422/16
[58] Field of Search ................ 436/55, 56; 422/62, 422/3, 16

[56] References Cited

U.S. PATENT DOCUMENTS

| | | | |
|---|---|---|---|
| 4,166,105 | 8/1979 | Hirschfeld | 436/536 |
| 4,374,102 | 2/1983 | Connelly et la. | 423/206.2 |
| 4,374,964 | 2/1983 | Phillips et la. | 525/540 |
| 4,783,314 | 11/1988 | Hoots et al. | 422/3 |
| 4,801,388 | 1/1989 | Fong et al. | 210/701 |
| 4,929,425 | 5/1990 | Hoots et al. | 422/13 |
| 5,128,419 | 7/1992 | Fong et al. | 525/351 |
| 5,171,450 | 12/1992 | Hoots | 210/701 |
| 5,216,086 | 6/1993 | Fong et al. | 525/351 |
| 5,260,386 | 11/1993 | Fong et al. | 525/340 |
| 5,294,664 | 3/1994 | Morrison, Jr. et al. | 524/560 |
| 5,435,969 | 7/1995 | Hoots et al. | 422/14 |

OTHER PUBLICATIONS

Mayer, The Chemistry of Natural Coloring Matters, Reinhold Publishing Corporation, 1943 pp. 117–118, 269, 315–318 and 155–156.

*Primary Examiner*—Jill Warden
*Assistant Examiner*—Alexander Markoff
*Attorney, Agent, or Firm*—Robert A. Miller; Kelly L. Cummings

[57] ABSTRACT

The invention comprises a method of determining the concentration of a water soluble polymeric treating agent added to wastewater treatment system. The method comprises several steps including dosing the body of water with a predetermined concentration of a treating agent having a fluorescent tag covalently bonded to the treating agent, removing a sample of the water containing the tagged treating agent, analyzing the emissivity of the sample to measure the concentration of the treating agent in the sample and adjusting the concentration of the treating agent accordingly to fit within a predetermined concentration range.

12 Claims, 3 Drawing Sheets

TAGGED EPICHLOROHYDRIN-DIMETHYLAMINE COPOLYMERS FOR USE IN WASTEWATER TREATMENT

The present application is a continuation-in-part of application Ser. No. 08/423,598, filed Apr. 17, 1995, now abandoned by Ananthasubramanian Sivakumar, Jitendrah T. Shah and Jeffrey R. Cramm, entitled "Tagged Epichlorohydrin-dimethylamine Copolymers for Use in Wastewater Treatment", the disclosure of which is incorporated herein by reference.

BACKGROUND OF THE INVENTION

1. Field of the Invention

The present invention is in the technical field of monitoring and controlling the dosage of cationically charged polymeric water treatment chemicals which are used in liquid/solids and liquid/liquid separation processes.

2. Description of the Prior Art

Cationically charged water soluble or water dispersible polymers are utilized in a variety of processes that involve the separation of solids or immiscible liquids dispersed or suspended in water from water, and the dewatering of solids containing water. These types of polymers, which may be natural or synthetic are broadly termed coagulants and flocculants. These polymers can be utilized in such diverse processes as emulsion breaking, sludge dewatering, raw water clarification, drainage and retention aids in the manufacture of pulp and paper, flotation aids in mining processing and color removal.

Polymers of this type generally work by neutralizing the anionic charge of the suspended solids, or liquids which are to be removed. These solids or liquids may be waste which must be removed from water, or desirable products which are recovered from aqueous systems such as, in the case of, for example, coal fines which can be coagulated or flocculated and sold as fuel.

In the water treatment field of solids/liquid separation, suspended solids are removed from water by a variety of processes, including without limitation, sedimentation, straining, flotation, filtration, coagulation, flocculation, emulsion breaking and the like. Additionally, after suspended solids are removed from the water they must often be dewatered so that they may be further treated or properly disposed. Liquids treated for solids removal often have as little as several parts per billion of suspended solids or dispersed oils or, may contain large amounts of suspended solids or oils. Solids being dewatered may contain anywhere from 0.25 weight percent solids, to 40 or 50 weight percent solids material. So called liquid solids separation processes are designed to remove solids from water, or, conversely and depending upon the desire component, liquids from solids.

While strictly mechanical means have been used to effect solids/liquid separation, modem methods often rely on mechanical separation techniques which are augmented by synthetic and natural cationic polymeric materials to accelerate the rate at which solids can be removed from water. These processes range from the treatment of raw water with cationic coagulant polymers which settle suspended inorganic particulates and make the water usable for industrial or municipal purposes. Other examples of these processes include, the removal of colored soluble species from paper mill effluent wastes, the use of organic flocculant polymers to flocculate industrial and municipal waste materials, recovering a sludge and emulsion breaking.

Regarding the mechanism of separation processes, particles in nature have either a cationic or anionic charge. Accordingly, these particles often are removed by a water soluble coagulant or flocculant polymer having a charge opposite to that of the particles. This is referred to as polyelectrolyte enhanced liquid/solids separation processes, wherein a water soluble or dispersible ionically charged polymer is added to neutralize the charged particles or emulsion droplets to be separated. The dosage of these polymers is critical to the performance of the process. Too little ionically charged polymer, and the suspended particles will not be charge neutralized and will thus still repel each other. Too much polymer, and the polymer will be wasted, or worse, present a problem in and of itself.

If the polyelectrolyte or ionically charged polymer being added is very effective for the given process, the polyelectrolyte that leaves with the water fraction generally represents an overdosage. More polyelectrolyte was added than required. If the polyelectrolyte being added is not very effective for the given process, significant amounts of polymer may leave the process with the water fraction as an indication of the polymers performance deficiencies. In either instance, a determination of the amount of polyelectrolyte that leaves a separation process with the filtrate or water fraction would be extremely beneficial. An effective polyelectrolyte should be added to a separation process in an amount just at or above that consumed by attachment to the solids or oil surfaces. Whether the dosage selected approaches this optimal dosage could be determined, and the dosage adjusted if necessary, if the level of the polyelectrolyte in the filtrate could be easily monitored. A less effective polyelectrolyte could be readily detected, and the polyelectrolyte selection changed if the level of the polyelectrolyte in the filtrate could be easily monitored.

Monitoring the concentration of polyelectrolyte in the filtrate is a formidable task not well suited to industrial applications. Analytical techniques such as colloid titration are complicated and time consuming and do not permit a real time result. Electronic instrumentation to determine charge is available, but such devices are expensive, and do not differentiate between charge associated with a polymer, or charge from other sources, including the water, solids, or other constituent in the effluent. Time consuming measurements are inefficient since the characteristics of a waste stream or emission may vary considerably with time.

The use of fluorescence emission spectroscopy to determine the concentration of a fluorescent chemical species is extremely rapid and sensitive, but the species being monitored must be fluorescent. A typical polyelectrolyte is not fluorescent or is not sufficiently fluorescent for monitoring by emission spectroscopy. Since the polyelectrolyte in its performance is consumed in the sense that it attaches to the solids and/or oils and is separated from the water therewith, adding a fluorescent signature chemical or tracer that follows the water would not reveal what fraction of the polyelectrolyte has been consumed, even if the concentration of the tracer can be correlated to polyelectrolyte dosage.

While determining polyelectrolyte dosage, for instance by adding a tracer in known proportion to the polyelectrolyte and monitoring the tracer concentration to determine if the target dosage or feed rate is being met, may in and of itself be of significant assistance, a water-soluble totally inert tracer is an indicator of only the theoretical zero-consumption concentration of the polyelectrolyte in the filtrate, and not the actual filtrate concentration of the polyelectrolyte. A signature chemical or tracer that itself preferentially follows the solids and/or oil likewise is not an indicator of polyelectrolyte consumption and hence polyelectrolyte performance.

It is therefore an object of this invention to provide a process for monitoring a polyelectrolyte water treatment chemical that is consumed in its performance, preferentially associating with one phase in a multiphase system.

It is an object of the present invention to monitor a polyelectrolyte that preferentially associates with one phase of a multiphase system by determining the extent of such preferential association.

It is an object of the present invention to determine the extent of preferential phase association of polyelectrolyte in a multiphase system using a technique that is rapid and sensitive. It is an object of the present invention to determine the extent of preferential phase association of a polyelectrolyte in a multiphase system using a technique that can be employed on a semi-continuous or continuous basis.

It is an object of the present invention to determine the extent of preferential phase association of a polyelectrolyte in a multiphase system using a technique that can be employed on line. It is an object of the present invention to determine the extent of preferential phase association of a polyelectrolyte in a multiphase system using a technique that determines the concentration of the polyelectrolyte in the non-preferred phase. These and other objects of the present invention are described in detail below.

SUMMARY OF THE INVENTION

The invention comprises a method of determining the concentration of a water soluble polymeric treating agent added to water in a once through system. The method comprises several steps including dosing the body of water with a predetermined concentration of a treating agent having a fluorescent tag covalently bonded to the treating agent, removing a sample of the water containing the tagged treating agent, analyzing the emissivity of the sample to measure the concentration of the treating agent in the sample and adjusting the concentration of the treating agent accordingly to fit within a predetermined concentration range.

DESCRIPTION OF THE PREFERRED EMBODIMENTS

Figure 1:
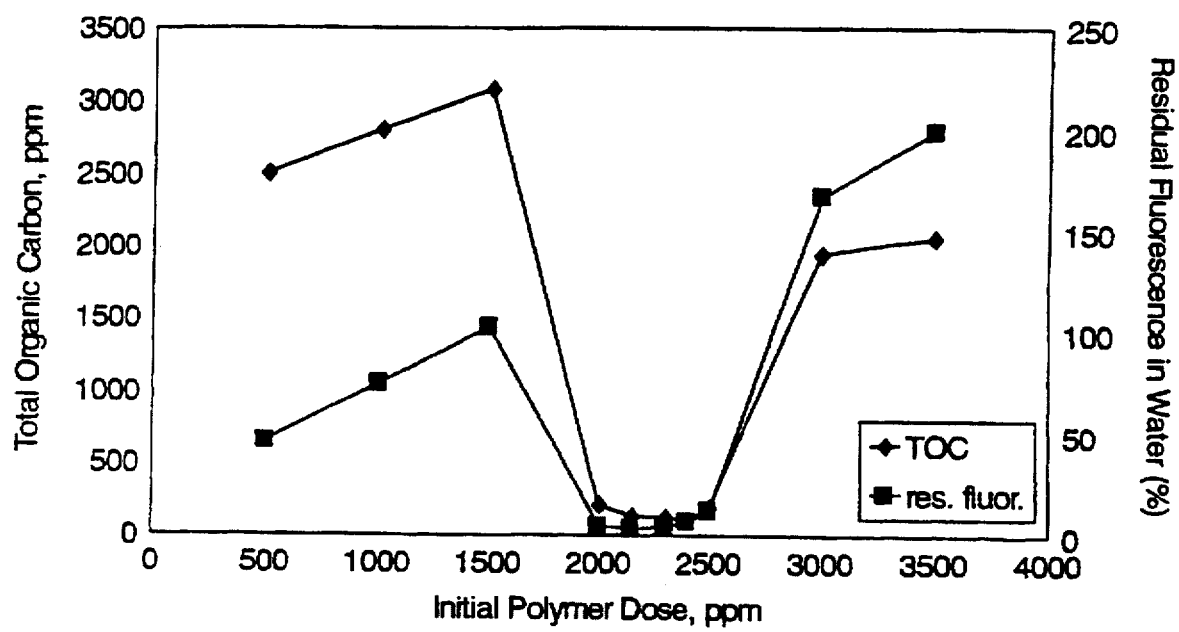
FIG. 1 is a graph comparing total organic carbon and residual fluorescence to initial polymer dose.

The method of the claimed invention comprises adding a water soluble polymeric treating agent to a wastewater and then measuring the concentration of that treating agent by means of analyzing the emissivity of fluorescent tags bonded thereto.

The use of polymeric treating agents containing chemical-bound fluorescent or light-absorbing labels allows the concentration monitoring control task to be completed in accordance with the present invention, even at very low polymer concentrations. The benefits of the invention are as follows:

(1) to achieve a continuous record of polymer concentration with respect to time and direct indication of whether polymer level is maintained within specified limits, (2) to allow feedback control of polymer level in order to maintain polymer concentration within specified limits, (3) to observe the response of an active treatment or product component (polymer) to changes in operating conditions of the system (e.g. effect of pH on wastewater color removal), (4) to accomplish performance responsive control of polymer level (e.g., if polymer level decreased due to increase in wastewater color, the monitor/feedback control equipment adds more to treatment to maintain a constant polymer level).

Polymers tagged with chemically-bound ultraviolet/visible light absorbing chromophores and fluorescent units are employed. These units can be incorporated into the polymer by covently linking an appropriately derivatized fluorescent species with an existing polymer,or by copolymerization with a fluorescent monomer.

Light-adsorbing chromophores can also be incorporated into the polymers by similar synthesis methods.

For maximum sensitivity, the label must have a large extinction coefficient for absorption combined with a high quantum yield of fluorescence. The emission band should be in a frequency range that has a minimum of interference from other species present in the water. Interfering species are expected to vary widely from one effluent stream to the next. The longer the wavelength of the emitted light, the less chance there is of encountering interference. High sensitivity allows low levels of label to be used so that the effect on polymer properties is minimized. The structure of the label can also be designed to have properties similar to the polymer itself.

With all of these factors in mind, a fluorescent group which fluoresces in the visible spectral range is used for labeling polymers. In particular, a derivative of the naphthalimide type dye is used. This derivative (I) is a di-tertiary amine to permit linear incorporation into polyamine backbones prepared by step polymerization.

This label combines high sensitivity with a dicationic structure once incorporated into the chain, which will minimize the effect on polymer properties. The emission maximum for this label is well out into the visible yellow range (>500 nanometers).

The bis(dimethylaminopropyl) functionalized dye (I) is reactive with epichlorohydrin. Sufficient dye was mixed with a dimethylamine solution for the synthesis of an epichlorohydrin-dimethylamine polymer containing 1.0 wt % of the fluorescent derivative. The dye was expected to incorporate linearly into the backbone of the polymer to give the following structure:

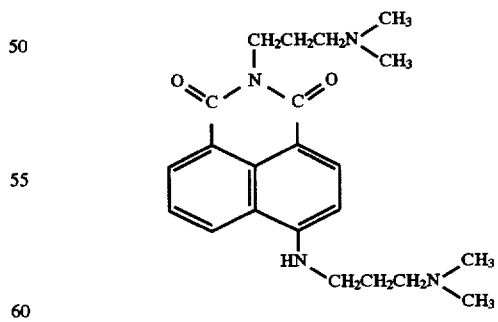

It should be noted that any fluorescent species containing amino groups which are sufficiently nucleophilic can react during polyamine synthesis and, therefore, can be used to prepare tagged polyamines. If the fluorescent species contains a monofunctional amine, it will be incorporated as a polymer end group. If the fluorescent species is difunctional, it can incorporate linearly into the backbone of the polyamine. If the fluorescent species contains tri- or greater functionality it can result in branched polyamines.

Examples of fluorescent species which, when modified to contain nucleophilic amino groups, can be used to prepare tagged polymers include: substituted aromatic hydrocarbons (e.g. naphthalenes, anthracenes, pyrenes, perylenes, stilbenes), substituted five-membered heterocyclic compounds (e.g. furans, thiophenes, pyrroles, oxazoles, oxadiazoles, thiadiazoles, pyrazolines, pyrazoles), condensed five-membered heterocyclic compounds (e.g. benzofurans, benzothiophenes, indoles, benzoxazoles, benzimidazoles, benzothiazoles, benzotriazoles, dibenzofurans, dibenzothiophenes, carbazoles), six-membered nitrogen heterocycles (e.g. pyridines, quinolines, acridines, pyrazines, qinoxalines, phenazines), six-membered oxygen heterocycles: zanthenes (e.g. fluoresceins, rhodamines), other six-membered heterocycles (e.g. benzoxanthenes, benzothioxanthenes, phenothiazines, phenoxazines), unsaturated ketones (e.g. anthrones benzanthrones, xanthones, thioxanthones, acridines, fluorenones, condensed quinones, indigoids, thioindigoids), and unsaturated acid derivatives (e.g. terephthalic acid esters, phthalic anhydride derivatives, coumarins, carbostyryls, oxazolones, naphthalimides).

Polyamine compounds according to the invention may be prepared using the following procedure. A fluorescent derivative is mixed with deionized water and an aqueous solution of amine compound in a PARR pressure reactor at 5° C. The reactor is then sealed and heated to 80° C. Finally, epichlorohydrin is pumped into the reactor over 2.5 hours while cooling the reacting mixture to maintain the 80° C. temperature. The reaction is then allowed to continue for two hours at 80° C. to complete polymerization.

The polyamine compounds of the invention are preferably chosen from water-soluble or water dispersible polymers which may be formed by step polymerization of materials such as epichlorohydrin-dimethylamine, ethylenedichloride-ammonia, ethylene-dichloride-methylamine-ammonia, epichlorohydrin-dimethylamine-ethylene oxide-propylene oxide and aniline-formaldehyde reacted with materials such as epichlorohydrin dimethylamine polymers, or any other step polymers which contain epichlorohydrin, dimethylamine, ethylenedichloride, ammonia, methylamine, ethyleneoxide, propyleneoxide, aniline-formaldehyde condensates, or any admixture of the above ingredients, so as to form a polymer which is water-soluble or water-dispersible.

The polyamine compounds of the invention preferably have an average molecular weight ranging between about 5,000 to about 250,000 daltons. Ethylenedichloride and ammonia react by a series of ammonolysis and alkylation steps to afford a polymer in which the two-carbon unit of ethylene dichloride and the nitrogen atom of ammonia alternate to form chain, branched, or crosslinked structures. Furthermore, the primary, secondary and tertiary nitrogen atoms in such structures may be quaternized by standard methods which are known to those skilled in the art. These polymers are discussed in detail in U.S. Pat. No. 4,374,964, the disclosure of which is incorporated herein by reference.

It is well-known that halohydrins such as epichlorohydrin may react with an amine, with combinations of several different amines, or with combinations of amines and ammonia to produce polyamines containing alternating nitrogen atoms and halohydrin fragments. The reactions leading to polymer formation are all nucleophilic substitutions of the amines or ammonia onto epoxides or chlorohydrins. The polymers are disclosed in detail in U.S. Pat. No. 4,374,102, the disclosure of which is incorporated herein by reference. The preparation of such materials is also discussed in detail in Canadian Patent No. 731,212, the disclosure of which is incorporated herein by reference.

The relative proportions of the polyfunctional amine and polyfunctional halohydrin employed in making the polymers for the purpose of the invention can be varied depending upon the particular types of amine and polyfunctional halohydrin and the reaction conditions. These polymers may also be quaternized using known methods.

Preferred polymers which are useful in the practice of the invention include the polymeric reaction products of the following reactions:

1. Ethylenedichloride and ammonia, including the associated methyl chloride and dimethyl sulfate quaternary amine salts (QUATS);
2. Epichlorohydrin (EPI) and dimethylamine (DMA);
3. Epichlorohydrin, dimethylamine and ethylenediamine, these include the associated methyl chloride or methyl sulfate QUATS;
4. Epichlorohydrin, dimethylamine and ammonia, including the associated methyl chloride or methyl sulfate QUATS;
5. Epichlorohydrin, dimethylamine and hexamethylenediamine, including the associated methyl chloride or methyl sulfate QUATS.

EXAMPLE 1

The tagged epi-DMA polymer was tested on an oil-in-water emulsion of an organophosphate ester.
Procedure The polymer was added to 100 ml of emulsion at different concentrations. The polymer was initially mixed at 300 rpm for two minutes and then mixed at 70 rpm for two minutes using a Phipps and Bird gang stirrer. The coagulated oil particles were allowed to settle for 10 minutes and the supernatant was then collected. The supernatant was filtered through a 0.45 micron filter and analyzed for the residual polymer fluorescence using a Gilford Fluoro IV fluorometer. The performance of the polymer was monitored by measuring the total organic carbon (TOC) of the filtrate using a Shimadzu total organic carbon analyzer.
Results The data obtained for the emulsion is shown in FIG. 1. The TOC and the residual polymer fluorescence are plotted as a function of initial polymer dose. As seen in FIG. 1, the residual fluorescence traces the TOC curve very well. The polymer dose can be optimized based on the change in the slope of the fluorescence curve.

EXAMPLE 2

The tagged epi-DMA was tested in color removal application on pulp and paper mill wastewater.
Procedure The polymer was added to 250 ml of the wastewater at different concentrations. The polymer was initially mixed at 330 rpm for 1 minute and then mixed at 60 rpm for 5 minutes using a Phipps and Bird gang stirrer. The precipitated and coagulated particles were allowed to settle for 10 minutes. The supernatant was collected and filtered through a 0.8 micron millipore filter. The filtrate was then analyzed for residual fluorescence using a Gilford IV fluorometer at an excitation wavelength of 450 nm and emission wavelength of 550 nm. In order to measure the true color, the pH of the supernatant was adjusted to 7.6 and then filtered through a 0.8 micron millipore filter. The filtrate was analyzed for true color by measuring the absorbance at 465 nm using a Hach DR 2000.

Results

Figure 2:
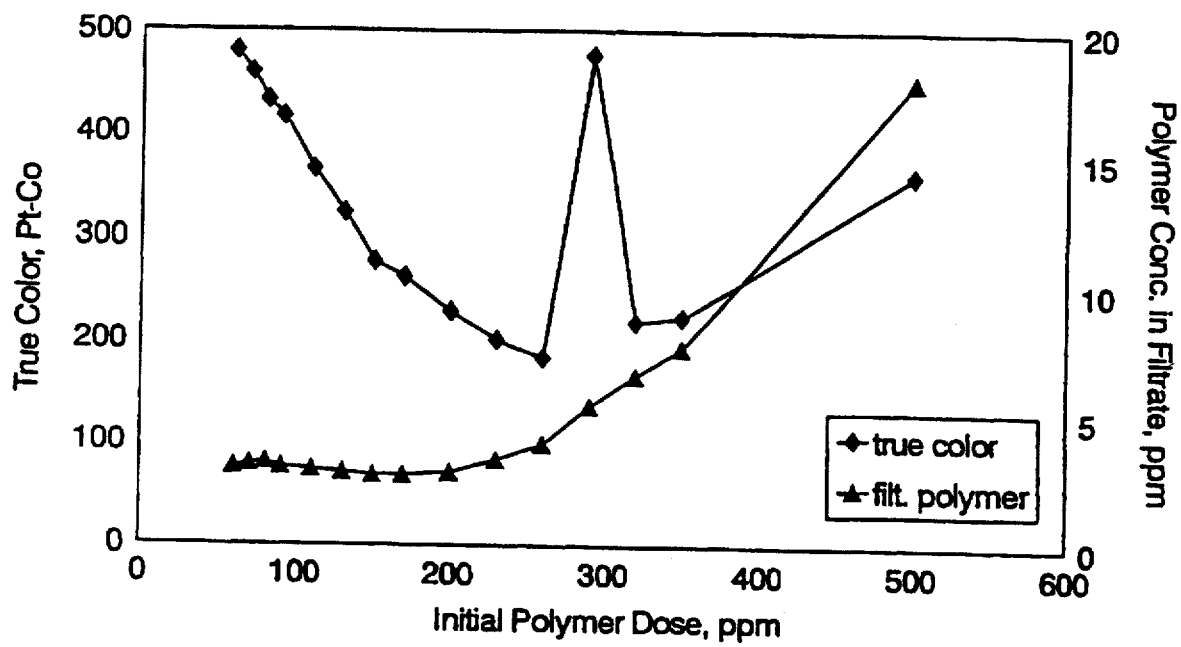
FIG. 2 is a graph comparing true color and polymer concentration in filtrate to initial polymer dose.
Figure 3:
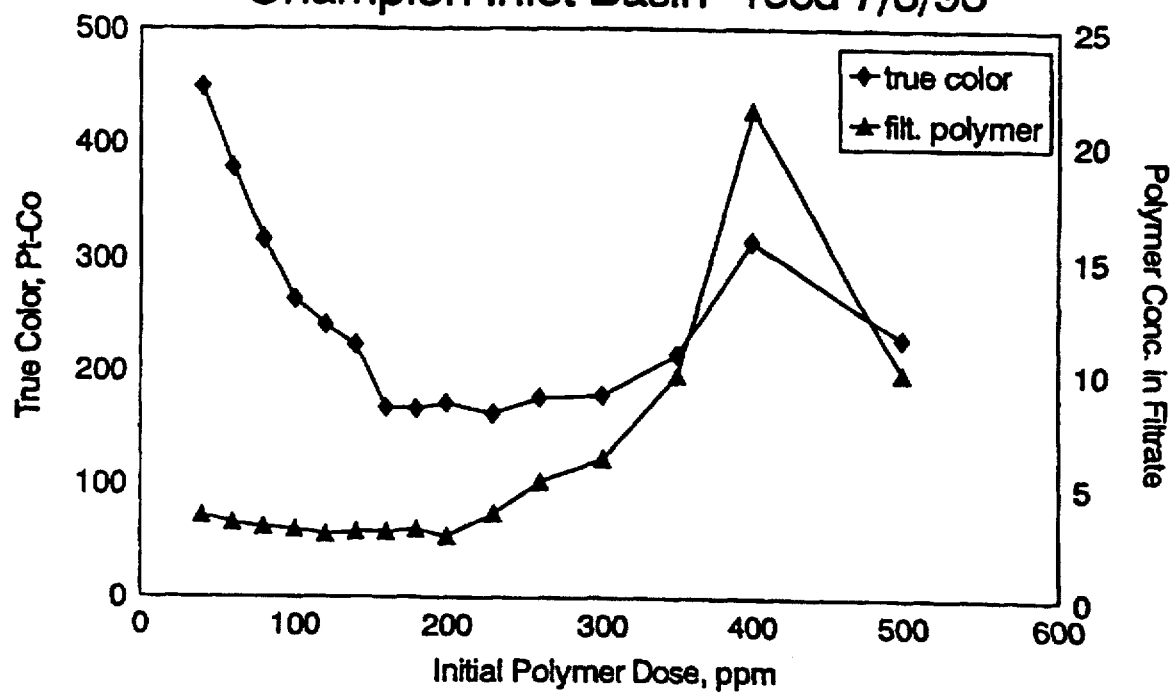
FIG. 3 is a graph comparing true color and polymer concentration in filtrate to initial polymer dose.

The results of the testing on two different batches of wastewater from Champion are shown in the attached FIGS. 2 and 3. The residual fluorescence in the filtrate correlates very well with the true color as a function of the polymer dose. The process will be optimized and controlled based on the slope change in fluorescence curve which occurs at the minimum in true color.

EXAMPLE 3

Preparation of tagged epichlorohydrin-dimethylamine polymer:

Fluorescent derivative I (1.4 grams), de ionized water (31.2 grams), and 61% aqueous dimethylamine solution (73.9 grams) were mixed in a PARR pressure reactor at 5 degrees C. The reactor was sealed and heated to 80 degrees C. Epichlorohydrin (93.5 grams) was pumped into the reactor over 2.5 hours while cooling the reacting mixture to maintain the temperature at 80 degrees C. The mixture was stirred at 80 degrees C. for 2 more hours to complete the polymerization.

Changes can be made in the composition, operation and arrangement of the method of the present invention described herein without departing from the concept and scope of the invention as defined in the following claims:

We claim:

1. Method for controlling a concentration of a water soluble polymeric treating agent added to wastewater comprising the steps of:
   a. adding to wastewater being confined in a once through wastewater treatment system a predetermined dose of a water soluble polymeric treating agent bearing a fluorescent moiety tag covalently bonded thereto, said wastewater containing liquid and solid portions;
   b. removing a sample of said wastewater containing said polymeric treating agent;
   c. separating the solid and liquid portions of said sample;
   d. measuring emissivity of the liquid portion of said sample as a measure of the concentration of the polymeric treating agent in the wastewater sample;
   e. continuously repeating steps (a) through (d) to monitor the emissivity as a function of the added amount of the polymeric treating agent; and
   f. adjusting the concentration of the polymeric treating agent in the wastewater according to the changes in slope of the emissivity versus the added dose of the polymeric treating agent.

2. The method of claim 1, wherein the water soluble polymeric treating agent is a water-soluble condensation polymer formed by step polymerization of materials selected from the group consisting of epichlorohydrin-dimethylamine, ethylenedichloride-ammonia, ethylenedichloride-methylamine-ammonia, epichlorohydrin-dimethylamine-ethylene oxide-propylene oxide, aniline-formaldehyde reacted with materials selected from the group consisting of epichlorohydrin dimethylamine polymers, and polymers which contain epichlorohydrin, dimethylamine, ethylenedichloride, ammonia, methylamine, ethyleneoxide, propyleneoxide, aniline-formaldehyde condensates and mixtures thereof.

3. The method of claim 2, wherein the water soluble polymeric treating agent is a polymer selected from the group consisting of a polymeric reaction product of:
   ethylenedichloride and ammonia including the associated methyl chloride and dimethyl sulfate quaternary amine salts thereof;
   epichlorohydrin and dimethylamine;
   epichlorohydrin, dimethylamine and ethylenediamine including the associated methyl chloride and methyl sulfate quaternary amine salts thereof;
   epichlorohydrin, dimethylamine and ammonia including the associated methyl chloride and methyl sulfate quaternary amine salts thereof;
   epichlorohydrin, dimethylamine and hexamethylenediamine including the associated methyl chloride and methyl sulfate quaternary amine salts thereof.

4. The method according to claim 1, wherein the fluorescent moiety tag is selected from the group consisting of substituted aromatic hydrocarbons, substituted five-membered heterocyclic compounds, condensed five-membered heterocyclic compounds, six-membered nitrogen heterocycles, six-membered oxygen heterocycles, xanthenes, other six-membered heterocycles, unsaturated ketones and unsaturated acid derivatives.

5. The method according to claim 4, wherein the substituted aromatic hydrocarbons are selected from the group consisting of naphthalenes, anthracenes, pyrenes, perylenes and stilbenes.

6. The method according to claim 4, wherein the substituted five-membered heterocyclic compounds are selected from the group consisting of furans, thiophenes, pyrroles, oxazoles, oxadiazoles, thiadiazoles, pyrazolines and pyrazoles.

7. The method according to claim 4, wherein the condensed five-membered heterocyclic compounds are selected from the group consisting of benzofurans, benzothiophenes, indoles, benzoxazoles, benzimidazoles, benzothiazoles, benzotriazoles, dibenzofurans, dibenzothiophenes and carbazoles.

8. The method according to claim 4, wherein the six-membered nitrogen heterocycles are selected from the group consisting of pyridines, quinolines, acridines, pyrazines, qinoxalines, phenazines.

9. The method according to claim 4, wherein zanthenes are selected from the group consisting of fluoresceins and rhodamines.

10. The method according to claim 4, wherein the other six-membered heterocycles are selected from the group consisting of benzoxanthenes, benzothioxanthenes, phenothiazines and phenoxazines.

11. The method according to claim 4, wherein the unsaturated ketones are selected from the group consisting of anthrones benzanthrones, xanthones, thioxanthones, acridones, fluorenones, condensed quinones, indigoids and thioindigoids.

12. The method according to claim 4, wherein the unsaturated acid derivatives are selected from the group consisting of terephthalic acid esters, phthalic anhydride derivatives, coumarins, carbostyryls, oxazolones and naphthalimides.

* * * * *

UNITED STATES PATENT AND TRADEMARK OFFICE
CERTIFICATE OF CORRECTION

PATENT NO. : 5,705,394
DATED : 1/6/98
INVENTOR(S) : Ananthasubramanian Sivakumar, Jitendra T. Shah, Jeffrey R. Cramm It is certified that error appears in the above-indentified patent and that said Letters Patent is hereby corrected as shown below:

On the title page: Item [75]

Inventors: Sivakumar Ananthasubramanian

SHOULD READ AS:

-- Inventors: Ananthasubramanian Sivakumar --

Signed and Sealed this

Fifth Day of January, 1999

Attest:

Attesting Officer

*Acting Commissioner of Patents and Trademarks*